United States Patent
Jackson et al.

[19]

[11] Patent Number: 6,116,238
[45] Date of Patent: Sep. 12, 2000

[54] DRY POWDER INHALER

[75] Inventors: Thomas R. Jackson; Karen Davies, both of San Diego; Jeff Chen, Palo Alto; Mike Ligotke, San Diego; Allan Cameron, Westlake Village, all of Calif.

[73] Assignee: Dura Pharmaceuticals, Inc., San Diego, Calif.

[21] Appl. No.: 08/982,320

[22] Filed: Dec. 2, 1997

[51] Int. Cl.[7] .......................... A61M 15/00; A61M 16/00; B05D 7/14; B65D 83/06

[52] U.S. Cl. ............................... 128/203.15; 128/203.12; 128/203.21

[58] Field of Search ........................ 128/200.14, 203.12, 128/203.15, 203.19, 203.21, 203.23

[56] References Cited

U.S. PATENT DOCUMENTS

| | | |
|---|---|---|
| D. 384,283 | 9/1997 | Davies et al. . |
| 4,307,734 | 12/1981 | Blankenship . |
| 4,627,432 | 12/1986 | Newell et al. ................... 128/203.15 |
| 4,778,054 | 10/1988 | Newell et al. ................... 128/203.15 |
| 4,811,731 | 3/1989 | Newell et al. ................... 128/203.15 |
| 4,860,740 | 8/1989 | Kirk et al. . |
| 5,035,237 | 7/1991 | Newell et al. ................... 128/203.15 |
| 5,207,217 | 5/1993 | Cocozza et al. ................. 128/203.21 |
| 5,327,883 | 7/1994 | Williams et al. ................ 128/203.12 |
| 5,372,128 | 12/1994 | Haber et al. . |
| 5,388,572 | 2/1995 | Mulhauser et al. . |
| 5,492,112 | 2/1996 | Mecikalski et al. ............. 128/203.15 |
| 5,497,764 | 3/1996 | Ritson et al. .................... 128/200.14 |
| 5,544,646 | 8/1996 | Lloyd et al. ..................... 128/200.14 |
| 5,577,497 | 11/1996 | Mecikalski et al. ............. 128/203.15 |
| 5,622,166 | 4/1997 | Eisele et al. . |
| 5,645,051 | 7/1997 | Schultz et al. . |

FOREIGN PATENT DOCUMENTS

| | | |
|---|---|---|
| 2 142 246 | 1/1985 | United Kingdom . |
| 2 242 134 | 9/1991 | United Kingdom . |

*Primary Examiner*—John G. Weiss
*Assistant Examiner*—Joseph F. Weiss, Jr
*Attorney, Agent, or Firm*—Lyon & Lyon LLP

[57] ABSTRACT

A dry powder inhaler has a slider for incrementally advancing a blister disk, to provide successive doses of a dry powder pharmaceutical. A blister disk is rotatably supported on a spindle on a deck plate of the inhaler. A powder port, an advancing slot, and a lifter slot extend through the deck plate. A slider is attached to the deck plate and movable between open and closed positions. As the slider is opened, a litter moves up on a ramp on the slider to shear open a blister, so that the blister contents can be mixed with air and inhaled. As the slider is moved back to the closed position, the lifter is withdrawn and an advancing finger turns the disk to bring the next blister into position for opening to provide the next dose to the patient.

15 Claims, 11 Drawing Sheets

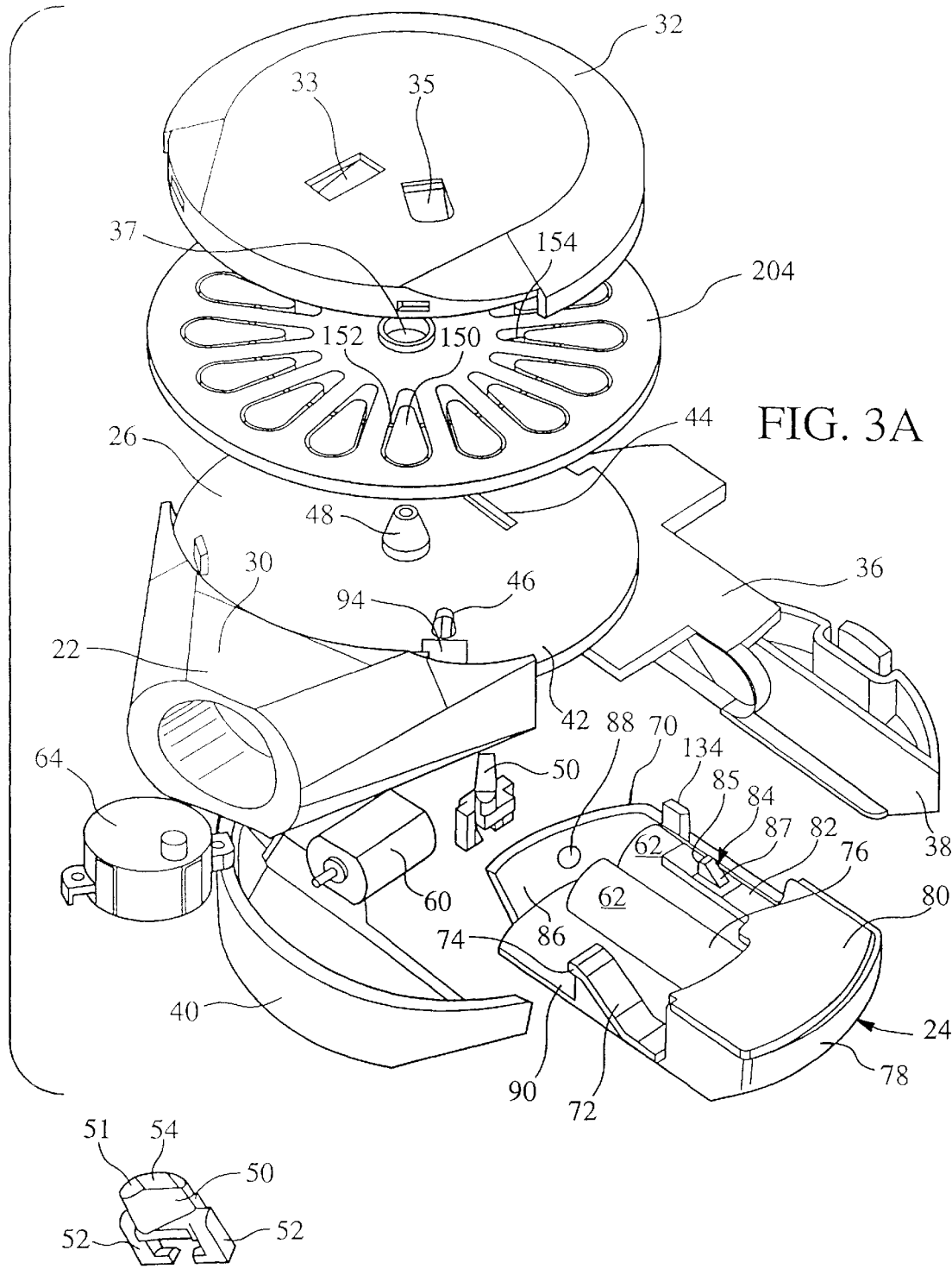

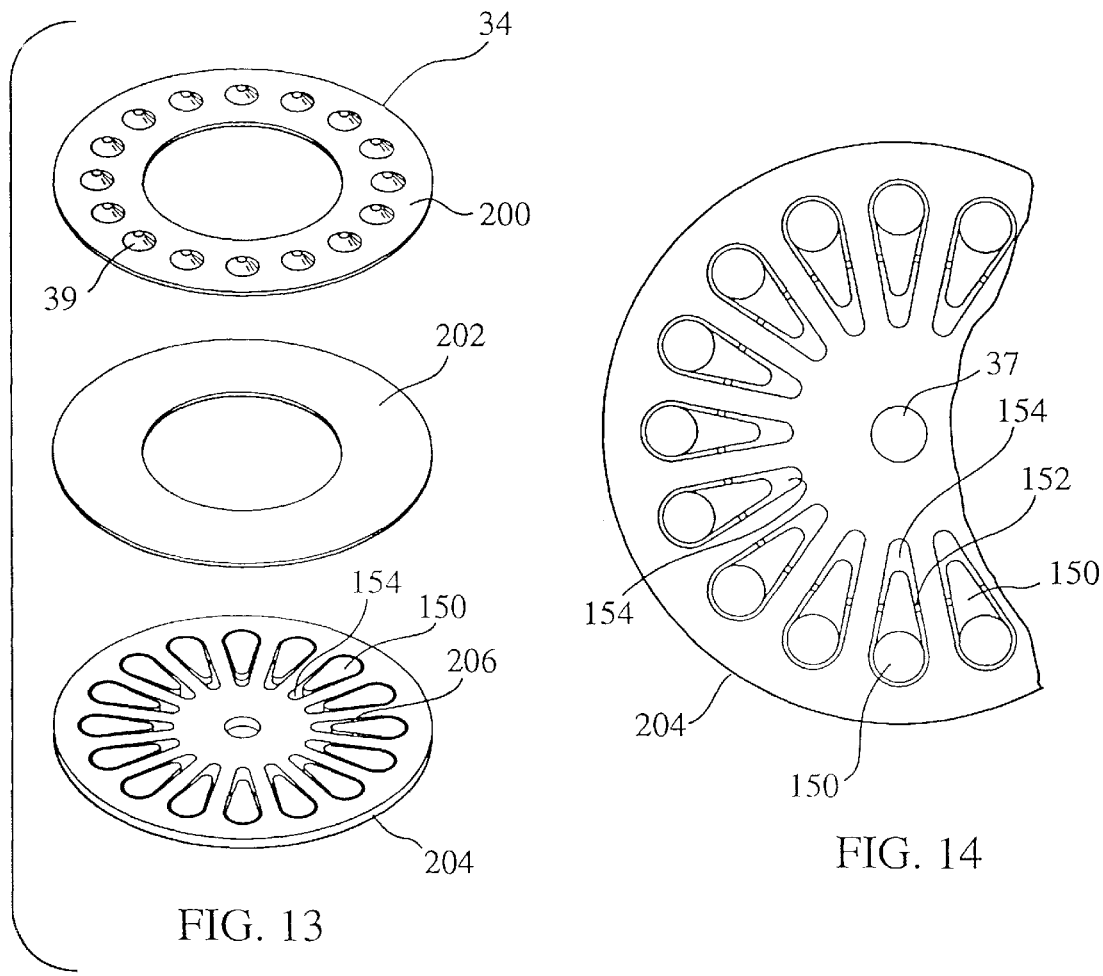
FIG. 13
FIG. 14
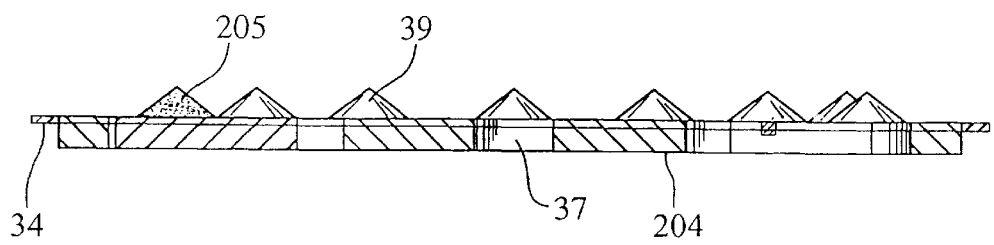
FIG. 15

DRY POWDER INHALER

BACKGROUND OF THE INVENTION

The field of the invention is inhalers for delivering dry powder drugs to the lungs.

Inhalers have long been used to deliver drugs into a patient's lungs. Typically, an inhaler provides a mixture of drugs and air or propellant gases. The mixture is delivered via the patient inhaling from a mouthpiece on the inhaler, for treatment of various conditions, for example, bronchial asthma. However, delivery of drugs via inhalation can be used for many other treatments, including those unrelated to lung condition.

Metered Dose Inhalers (MDIs) have been widely used for many years. MDI's typically dispense a single dose of a drug together with a propellant gas, with each actuation of the device. However, the propellant gases have been linked to destruction of the earth's ozone layer. In addition, with MDI's, the drug is generally released upon actuation of the device, regardless of whether the patient is properly inhaling during release. The patient may therefore not receive a complete dose unless the patient coordinates inhalation with actuation of the device. Achieving this coordination may be difficult for young children, or for patients with disabilities or under duress. Dry powder inhalers, on the other hand, do not have these disadvantages. Still, with dry powder inhalers, technical challenges remain in providing a reliable and simple to use device which can consistently deliver correct dosages of drugs.

One well known dry powder inhaler, the Diskhaler, described in U.S. Pat. No. 4,627,432, uses individual drug doses sealed within blisters on a blister disk. A plunger pierces the blisters, to release each dose. The disk is advanced by a knob with each successive dose. The Spiros inhaler, described in U.S. patent application Ser. No. 08/681,103 (incorporated herein by reference) is a dry powder inhaler which also uses a blister disk. Blisters are opened via shear tabs on the blister disk. The disk is advanced to provide the next dose by sliding the mouthpiece cover between open and closed positions. While these types of devices may have met with varying degrees of success, disadvantages remain in indexing or advancing a blister disk within an inhaler, with opening the blisters to access the drug contents, with reliably providing intended dosages, and in other areas.

Accordingly, it is an object of the invention to provide an improved dry powder inhaler.

SUMMARY OF THE INVENTION

To these ends, a drug dose carrier, such as a blister disk, is advantageously rotatably supported on or in a dry powder inhaler for pharmaceuticals. A slider is preferably attached to a housing or deck plate of the inhaler, and is movable between opened and closed positions. The slider may advantageously contain batteries or other electronic components electrically linked to components positioned in the main body of the inhaler via a flex circuit. Movement of the slider between the open and closed positions, in a preferred embodiment, opens a container on the carrier disk to release a pharmaceutical powder for inhalation. Preferably, this movement also advances the carrier, in preparation for delivery of a subsequent dose. Other objects, features and advantages will appear hereinafter.

BRIEF DESCRIPTION OF THE DRAWINGS

In the drawings, wherein similar reference characters denote similar elements throughout the several views:

FIGS. 3A and 3B are exploded top and bottom perspective views of the inhaler shown in FIGS. 1 and 2;

FIG. 4C is a perspective view of the lifter shown in FIG. 4A;

FIG. 13 is an exploded perspective view of a blister disk;

FIG. 14 is a top view thereof; and

FIG. 15 is a section view thereof.

DETAILED DESCRIPTION OF THE DRAWINGS

Figure 1:
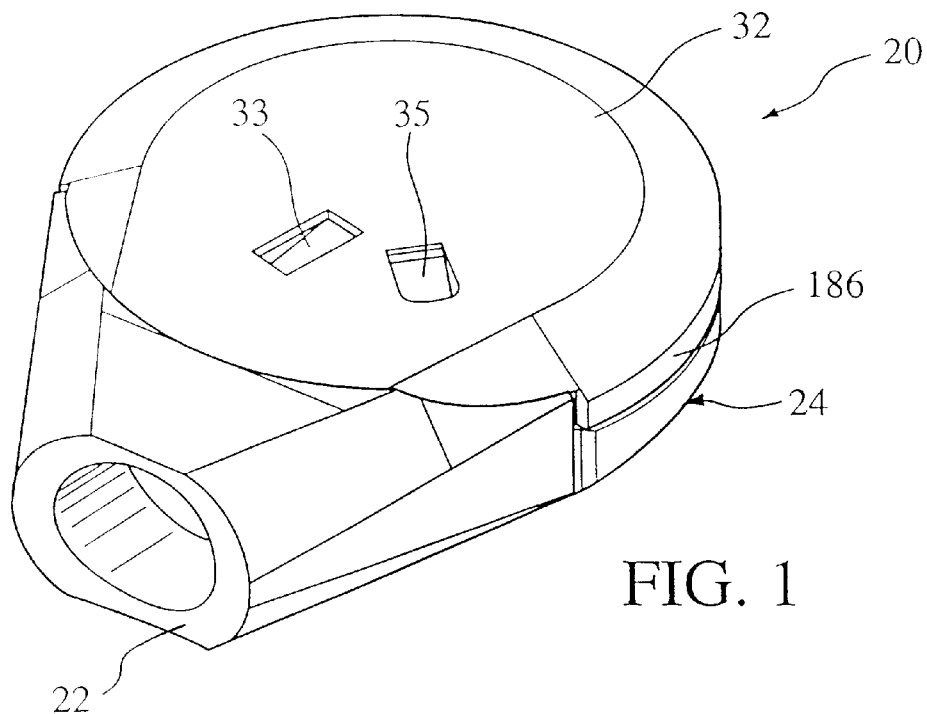
FIG. 1 is a perspective view of the inhaler of the invention with the slider in the closed or first position.
Figure 2:
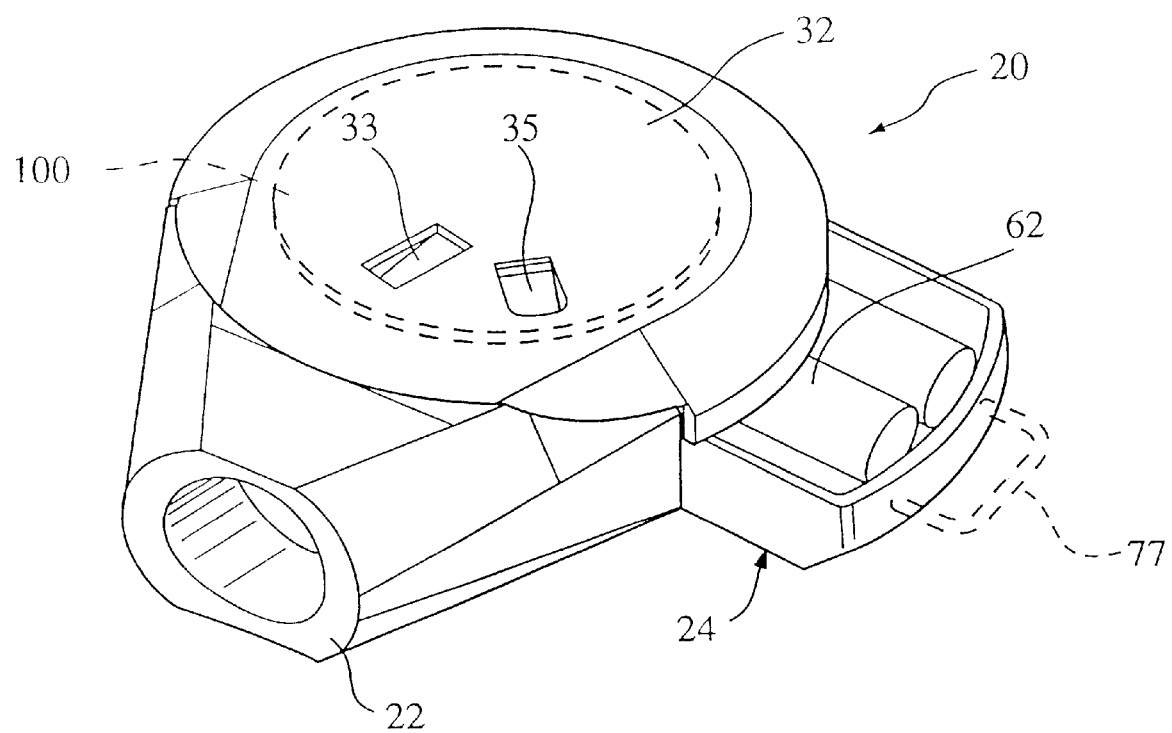
FIG. 2 is a perspective view thereof with the slider in the open or second position.

Turning now in detail to the drawings, the inhaler 20 includes a mouthpiece 22, and a slider 24, movable between a closed position, as shown in FIG. 1, and an open position as shown in FIG. 2. A handle 77 may be provided on the slider 24.

Turning to FIGS. 3A, 3B and 5–7, a deck plate 42 has a flat top surface 26 and a flat bottom surface 28. A spindle 48 extends upwardly from the top surface 26 of the deck plate 42. A lifter slot 46 passes through the deck plate 42. An advancing slot 44 extends through the deck plate parallel to the direction of motion of the slider 24. A blister disk 34 used with the inhaler 20 includes a plurality of drug containing blisters 39 mounted on tabs 150, as described, for example, in U.S. Pat. No. 5,622,166, incorporated herein by reference.

Turning momentarily to FIGS. 13, 14 and 15, the blister disk 34 is made of a metal foil ring 200 having generally conical blisters 39 radially and equally spaced apart. The metal foil ring 200 and a seal ring 202 are adhered or bonded onto a carrier disk 204. The disk 204 is preferably plastic. The carrier disk 204 has tabs 150 pivotably attached to the disk 204 via flex joints 152. A blister 39 is aligned over each tab 150. The flex joints 152 hold the tabs 150 into a flat, in-plane position, but allow the tabs 150 to pivot about the flex joints 152, with nominal torque. As shown in FIG. 15, powdered drug 205 is contained within each blister 39.

A cover 32 is attached over the top surface of a blister disk 34 to form a cover/disk assembly or unit 45. The blister disk 34 has a central opening 37 so that it can be mounted on and rotate around the axis of the spindle 48 which is normal to the axis of motion of the slider. The cover 32 itself latches onto the deck and does not rotate. The cover 32 retains the blister disk onto the deck as the blister disk rotates.

Figure 6:
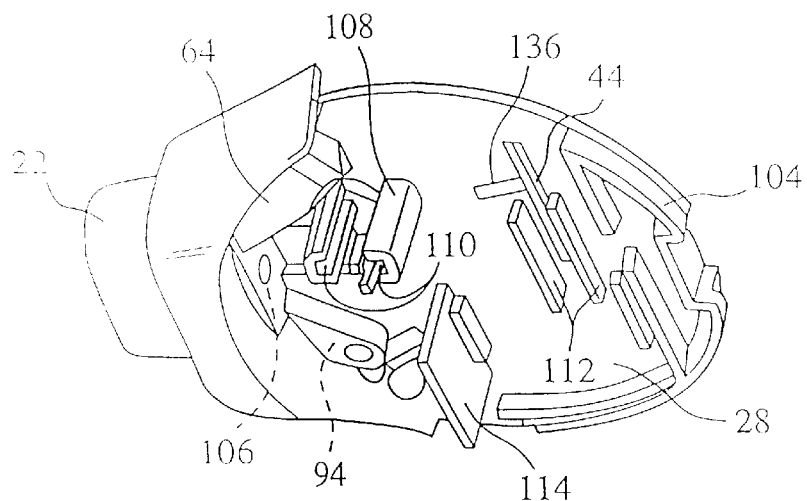
FIG. 6 is a bottom perspective view thereof.
Figure 7:
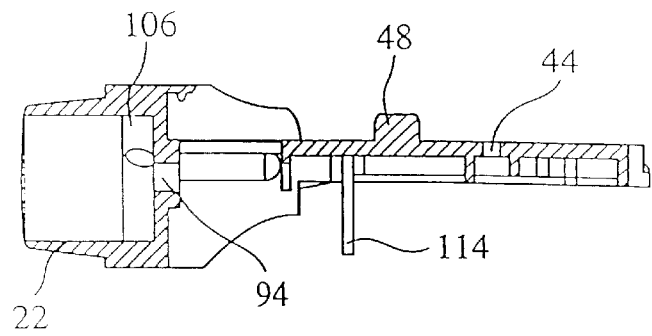
FIG. 7 is a section view thereof taken along a lateral centerline.

Referring specifically to FIGS. 3B and 5–7, a back rim 104 extends downwardly from the deck plate 42, opposite from the mouthpiece 22. A recess 102 in the deck plate 42 and back rim 104 allows for the motion of a latch 55 to lock the disk/cover assembly 45 onto the inhaler 20 when the cover blister disk assembly 45 is replaced by the user. A slider guide plate 114 extends downwardly from the bottom surface 28 of the deck plate 42. Slider lever guides 112 similarly are positioned on the bottom surface 28 of the deck plate 42, parallel to the advancing slot 44. Lifter guides 108 forming leg slots 110 are also attached to the bottom surface 28 of the deck plate 42 under the lifter slot 46, as best shown in FIG. 6. The leg slots 110 define the degree of freedom for the lifter motion.

A powder port 94 extends downwardly through the deck plate 42 and into an air passage 92 formed on the underside of the deck plate 42, heading to an aerosolizing or mixing chamber 106. The mouthpiece is advantageously removably attached to the deck plate 42. The spindle 48, back rim 104, slide guide plate 114, lever guides 112, and lifter guides 108 are preferably integral with the deck plate.

Referring back to FIGS. 3A, 3B, 4A and 4B, the slider 24 includes a slider frame 70 attached to a bottom plate 90, forming a battery compartment 76. A lifter ramp 72 is attached or formed along one side of the slider bottom plate 90. A lifter 50, as shown in FIGS. 4A, is slidably attached to the ramp 72. The lifter 50 includes L-legs 52 for holding the lifter 50 onto lips 74 on the ramp 72 and for retracting the lifter 50 from its raised position. The lifter 50 has a flat top surface 51 and an angled surface 54. The lifter ramp 72 passes under the lifter 50 as the slider 24 moves in and out. The lifter ramp 72 defines the cam profile which induces vertical motion in the lifter 50 as a result of the horizontal motion of the slider 24.

Figure 3B:
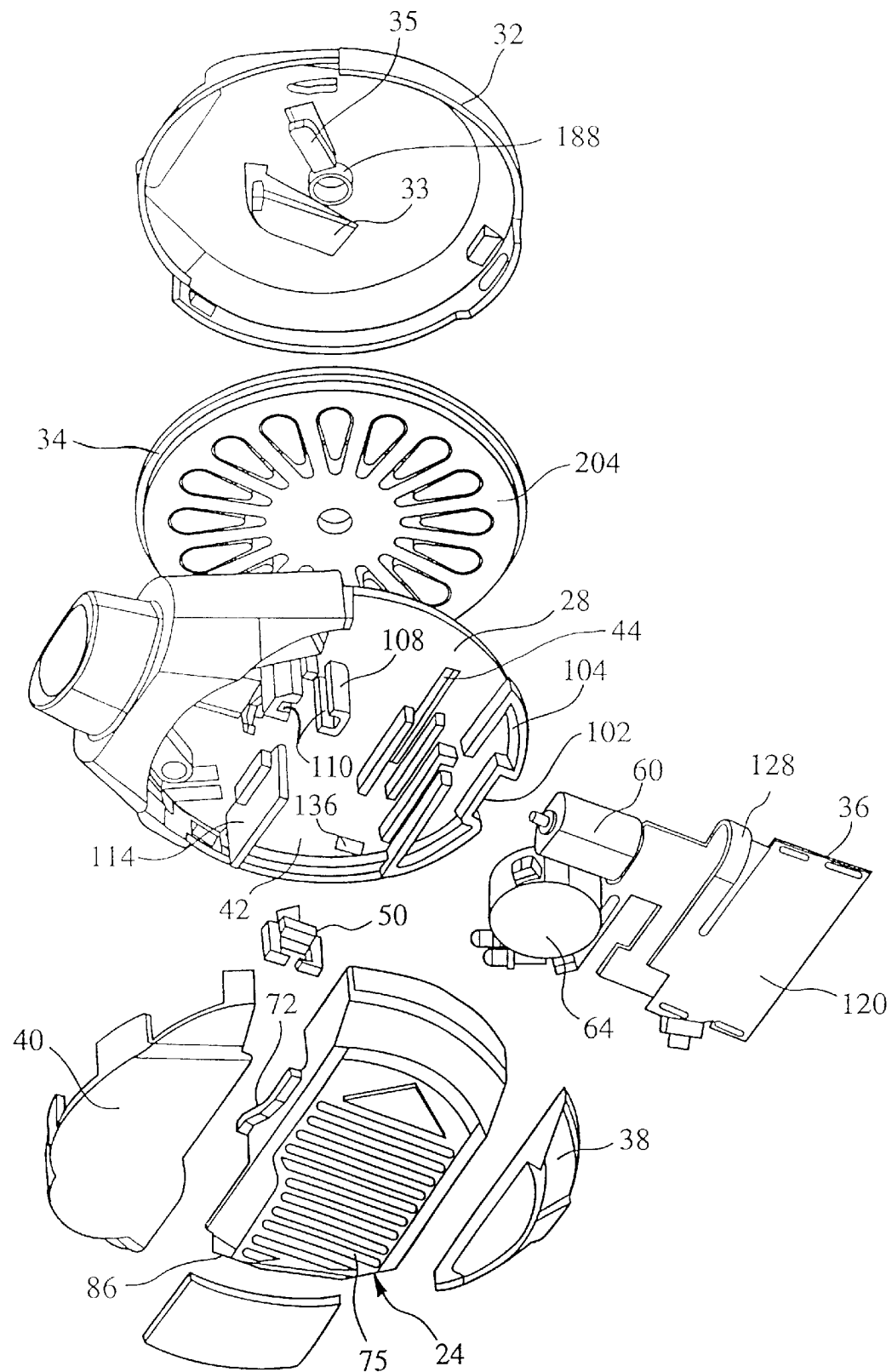
Figure 4A:
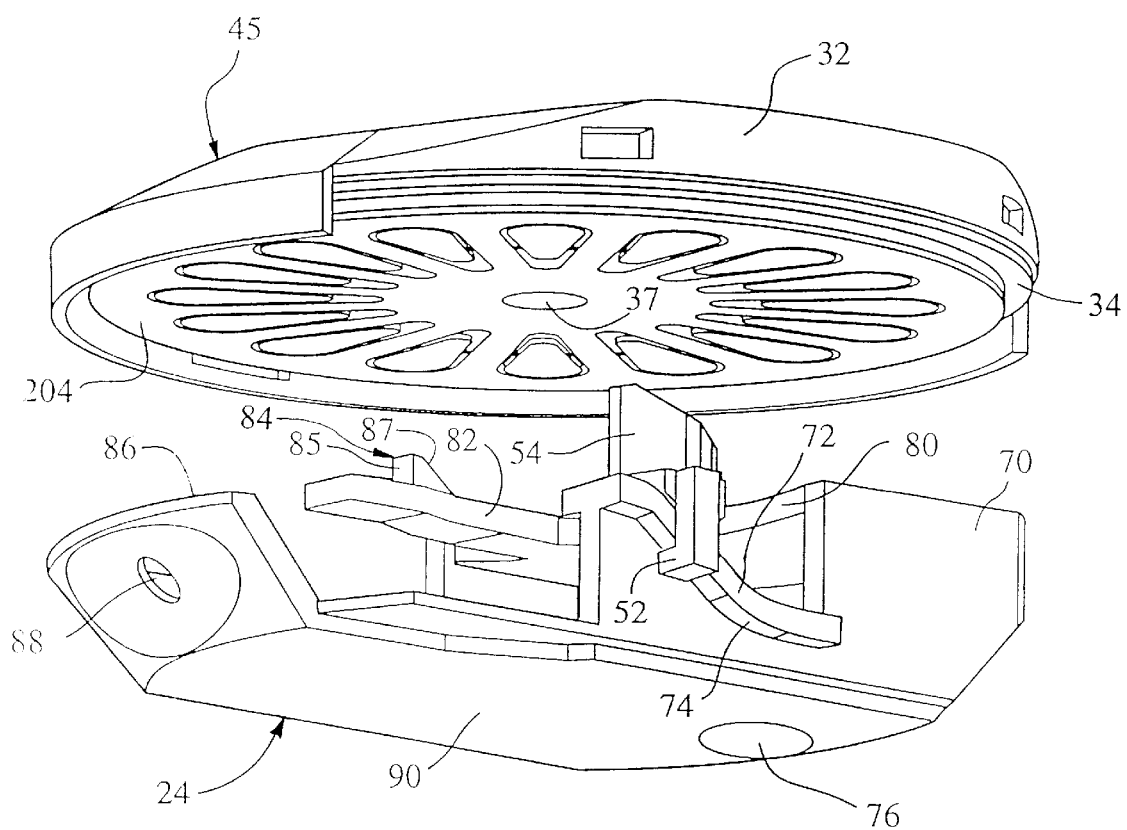
FIGS. 4A and 4B show enlarged perspective views of components of the inhaler of FIGS. 3A and 3B.
Figure 4B:
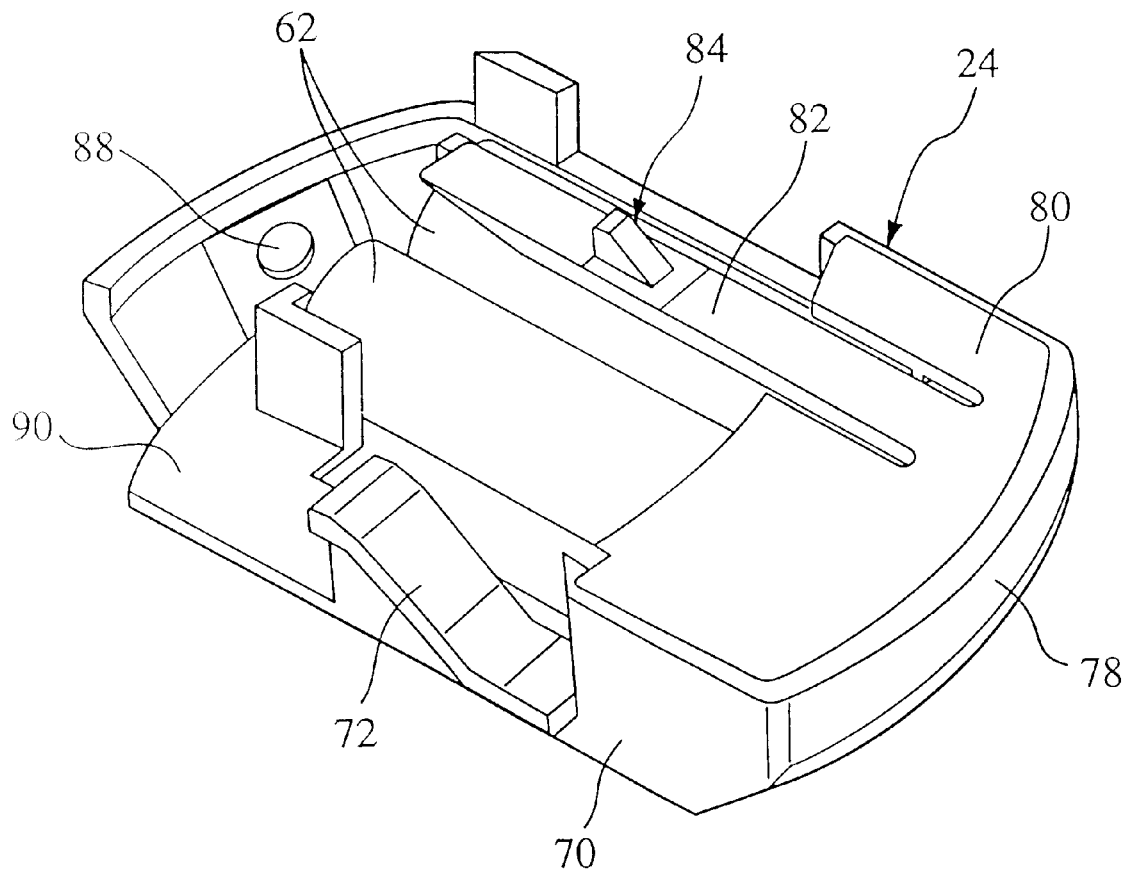
Figure 5:
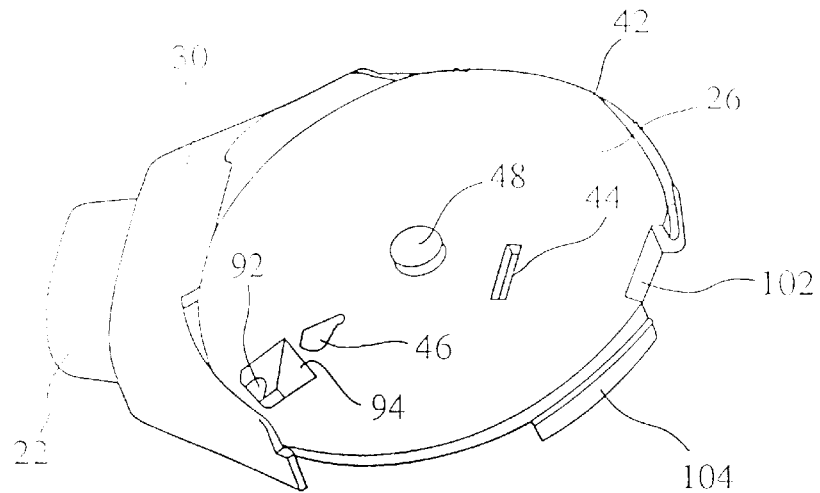
FIG. 5 is a top perspective view of the deck plate shown in FIGS. 3A and 3B.

Referring to FIGS. 3A, 4A and 4B, a slider cover plate 80 is attached to the slider frame 70, at the front or outside end 78 of the slider. A leg 82 on the slider cover plate 80 extends inwardly toward the rear end 86 of the slider 24. A spring biased or resilient advancing finger 84 having a flat back surface 85 and an angled front surface 87 projects upwardly from the leg 82. A battery check button extends through an opening 88 in the rear end 86 or bottom side 90 of the slider. As shown in FIGS. 3A and 3B, a rear housing section 38 and a front housing section 40 are attached to the bottom surface of the deck plate 42, on either side of the slider 24, to enclose the inhaler and capture the slider in its guides, allowing only one degree of freedom. The front end 78 and rear end 86 of the slider are preferably shaped to match the contours of the inhaler.

A mechanical stop 134 on the slider engages a ledge 136 on the deck plate, to limit the outward sliding movement of the slider. Finger ridges or gripping features 75 may be provided on the bottom of the slider, as shown in FIG. 3B.

Figure 8:
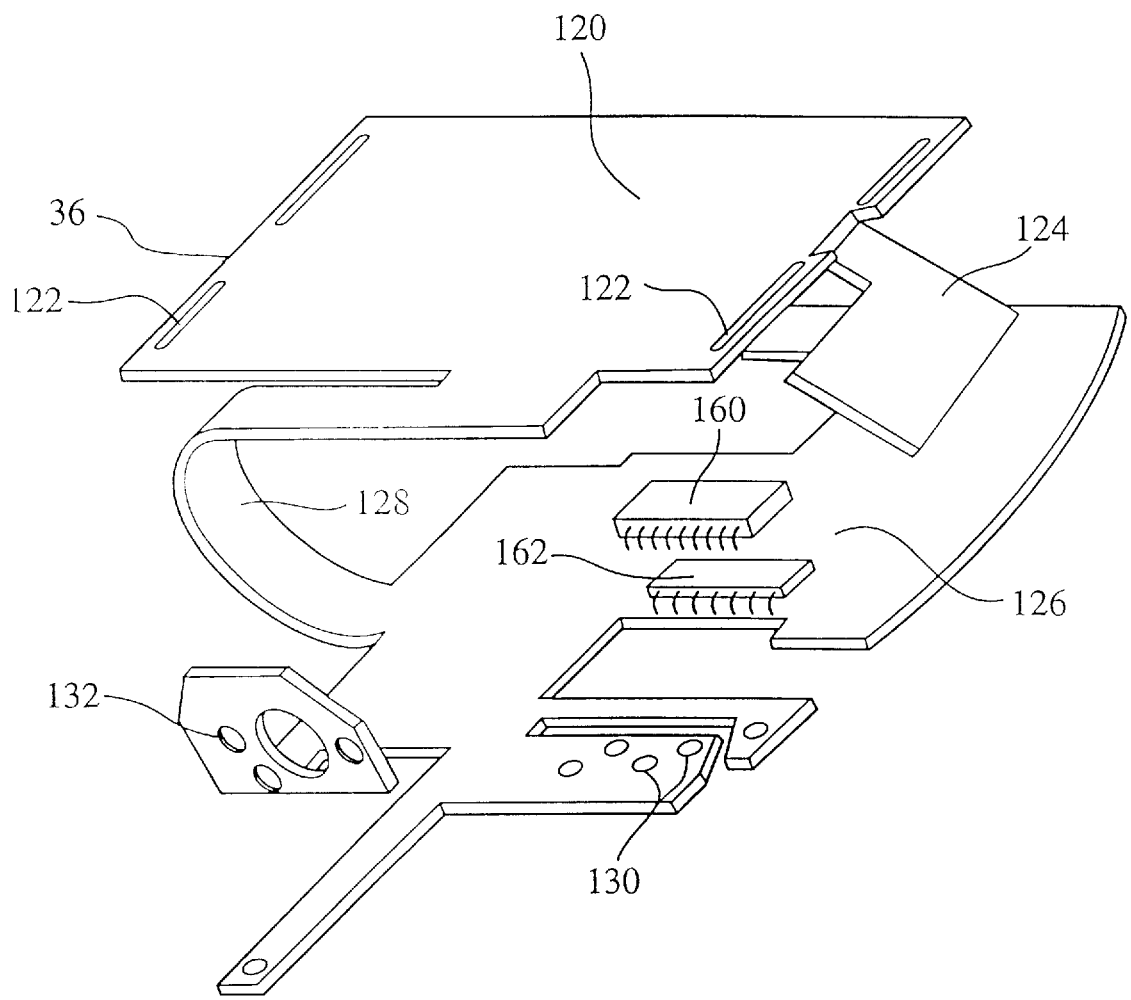
FIG. 8 is a perspective view of the flex circuit shown in FIGS. 3A and 3B.
Figure 9:
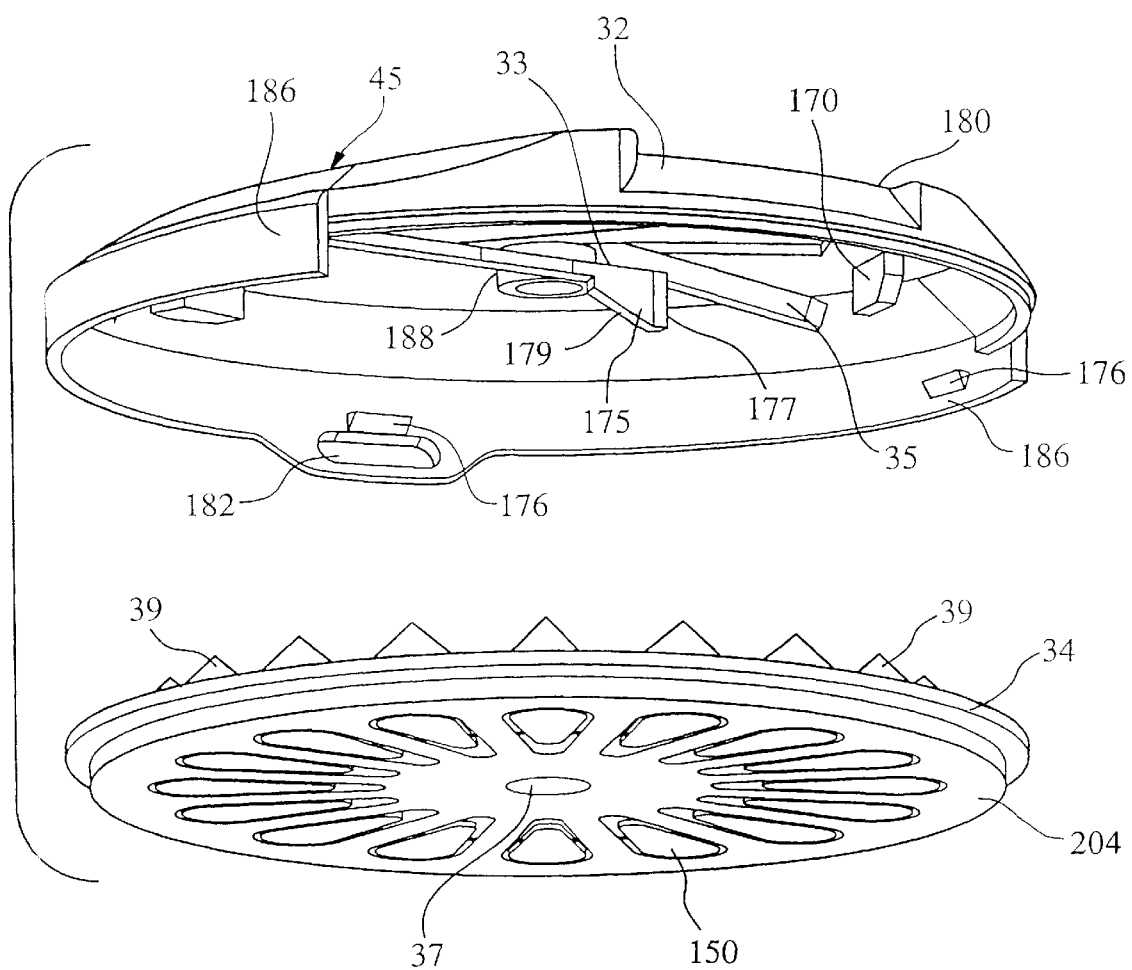
FIGS. 9 and 10 are perspective views of the disk and cover shown in FIGS. 3A, 3B and 4A.

Referring to FIGS. 3A, 3B and 8, a flex circuit 36 includes a battery plate 120 having battery slots 122. A circuitry area 126 is electrically connected to the battery plate 120 by a flexible ribbon 128. A switch 124 projects from the battery plate 120. An LED plate 130 and a motor lead tab 132 are provided as part of the circuitry area 126. A microprocessor 160 and memory chip 162 are provided on the circuitry area.

Turning to FIGS. 9–12, a blister crushing rib 170 projects downwardly from the underside of the cover 32. The crushing rib 170 is positioned so that when the cover/blister disk assembly 45 is assembled onto the inhaler 20, the rib 170 aligns just behind the powder port 94. A tab return spring 35 extends downwardly inside the cover 32. The tab return spring 35 pushes downwardly on the inner end of the tab on the blister disk 34, which is aligned over the lifter 50 and lifter slot 46. An anti-backup pawl 33 also extends down inside the cover 32. The pawl 33 has a foot 175 with a flat front surface 177 and an angled or ramp rear surface 179.

Disk clips 176 having angled bottom facing surfaces are spaced apart around the inside of the cover 32, on a cylindrical rim wall 186. A front latch 180 and a rear latch 182 are provided for attaching the cover 32 to the inhaler 20. Various latch designs may be used. Turning momentarily to FIG. 3A, the front latch fits into or engages a raised area 30 between the mouthpiece 22 and the disk assembly 45.

Figure 10:
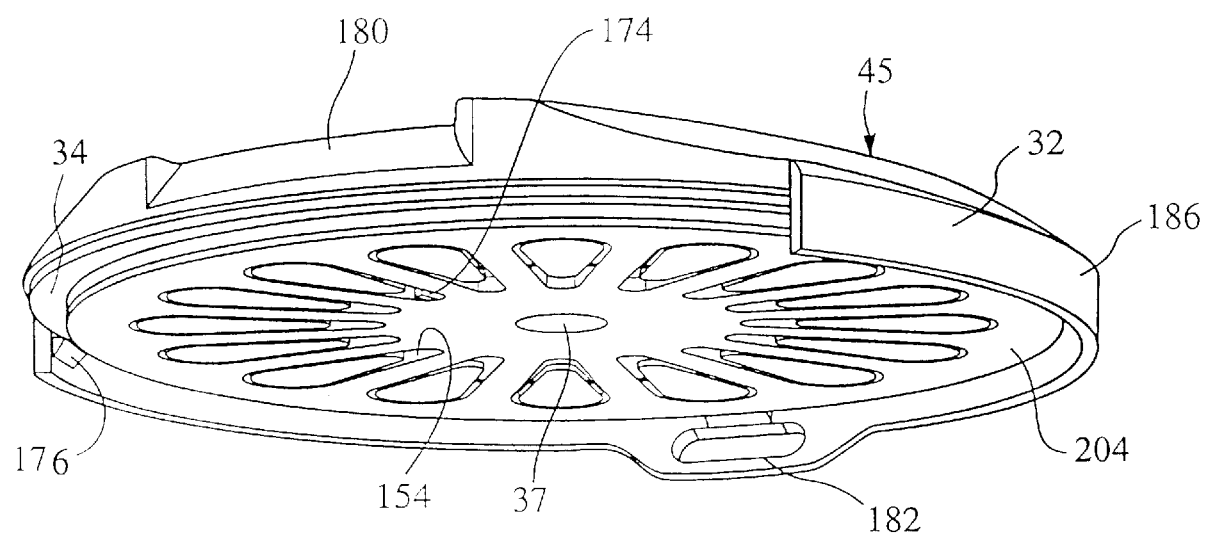
Figure 11:
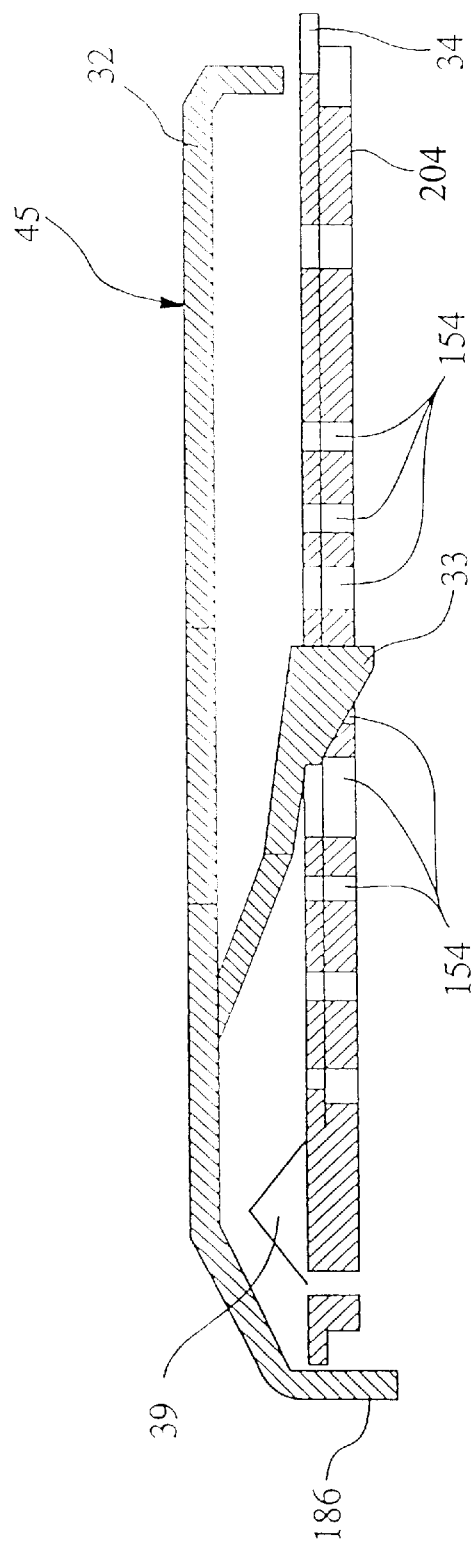
FIG. 11 is a cross section view thereof taken through the anti-back up pawl shown in FIG. 9.
Figure 12:
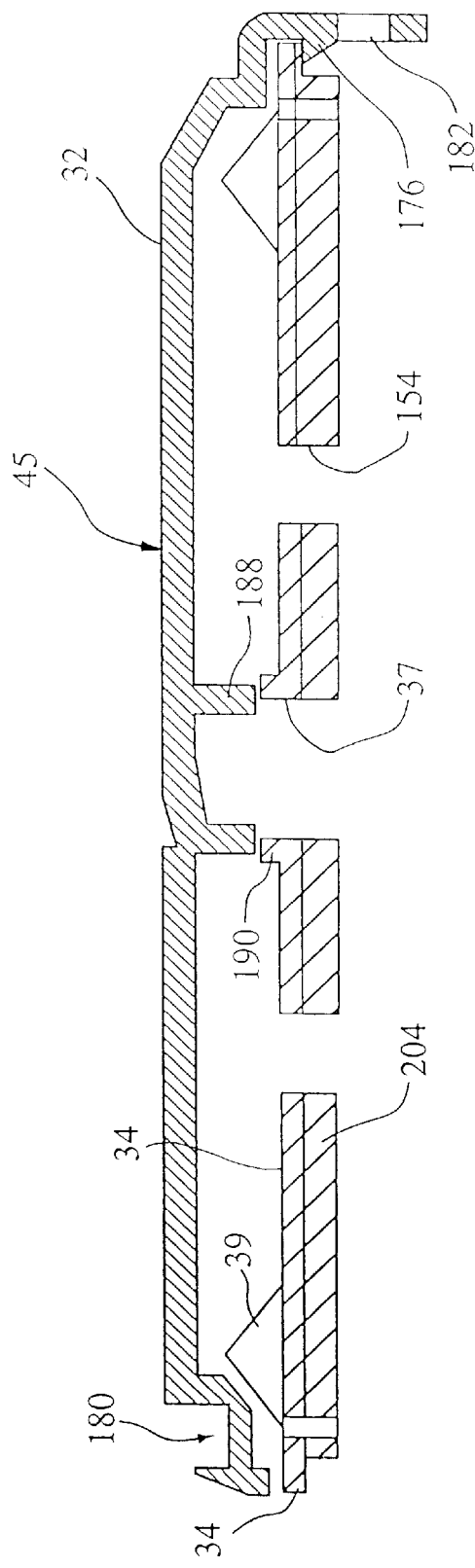
FIG. 12 is a central cross section thereof.

Referring to FIGS. 10 and 12, a central hub 188 extends down from the center inside surface of the cover 32. A blister disk 34 and a cover 32 are attached together to form an assembly 45 by aligning the central opening 37 or disk hub 190 of the disk with the hub 188 on the cover, and then pressing the disk into the cover. As this occurs, the clips 176 spring slightly apart, due to the natural resiliency of the cover material, and then snap back into place, thereby holding the disk and cover together. Once they are snapped together, they are substantially permanently yet rotatably attached to each other. As shown in FIG. 12, the disk 34 may have a perimeter recess 208, such that the disk clips 176 clip onto a perimeter lip 210 around the outside of the disk.

As shown in FIG. 12, the disk hub 190 and cover hub 188 generally align but do not necessarily engage each other. The disk 34 floats somewhat in the cover. When installed, the disk centers itself on the spindle 48.

Referring once again to FIGS. 3A and 3B, an electric motor 60 is connected to batteries 62 in the slider 24 via the battery plate 120, ribbon 128 and circuitry area 126 and motor lead tabs 132, which have electrical conductors within them. A breath actuated switch or sensor 64 also attached to the deck plate 42 and flex circuit senses pressure at the mouthpiece 22, and in response to sensed inhalation signals a microprocessor 160, which switches on the motor 60. The motor 60 spins an impeller within the mixing chamber 106, as described in U.S. Pat. No. 5,577,497, incorporated herein by reference.

A label 100, shown in phantom line in FIG. 2, may be attached to the top of the cover 32, to identify its contents, and to close off the openings where the pawl 33 and return spring 35 attach to the cover.

In use, the blister disk 34 is provided as an assembly 45 with the cover 32 attached. The cover 32 captures the blister disk 34 and secures them together. Hence, the cover 32 and blister disk 34 are handled as a unit or assembly by the patient. The cover protects the top and sides of the blister disk 34 from damage during handling. The patient attaches the cover/disk assembly 45 to the inhaler 20 via a bayonet, latch, rocker, or other attachment feature, such as the latches 180, 182. The cover 32 allows the blister disk 34 to rotate on the spindle 48 while the cover itself is irrotatably snapped onto the deck plate. The cover is oriented so that the tab return spring 35 is located over the lifter slot.

With the cover/blister disk unit 45 secured to the inhaler 20 on top of the deck plate 42, the inhaler 20 is ready for use. The patient pulls the slider 24 from the first or closed position shown in FIG. 1 to the second or open position shown in FIG. 2. Sliding movement of the slider is guided by the lever guides 112 and slider guide 114 and the covers 40 and 38. Finger grips 75 or a handle 77 may be provided on the slider 24 to better facilitate pulling the slider out. The slider 24 moves out until the mechanical stop 134 on the slider frame 70 contacts the stop or ledge 136 on the deck plate 42.

As the slider 24 is withdrawn, the lifter 50, which is held in position by the lifter guides 108, rides up on the lifter ramp 72. This ramp lifting movement causes the angled top surface 54 of the lifter 50 to rise up and protrude through the lifter slot 46 in the deck plate 42. The flat top surface 51 of the lifter 50 pushes against the underside of a tab 150 on the blister disk 34, causing a blister positioned over the tab to shear open, as the tab pivots about flex joints 152 which attach the tab to the disk 34. As the tab pivots, the angled surface 54 of the lifter engages the tab and continues to pivot it about the joints 152. As the blister shears open, the powdered pharmaceutical 205 contained within the blister falls into the powder port 94 and air passage 92, as described in U.S. Pat. No. 5,622,166.

As the slider 24 is pulled out to the open position, the advancing finger 84 also moves down under the deck plate 42, as it recedes out of the advance slot 44.

The lifter 50 is restrained against lateral or longitudinal movement, by the engagement of the L-legs around the lips 74 on the lifter ramp 72 and by the lifter guides 108. Accordingly, the lifter 50 can move only vertically up or down.

The patient then inhales on the mouthpiece 22. The inhalation is sensed by the pressure switch 64 which turns on the motor 60. The motor spins the impeller within the mixing chamber 106 creating an aerosol of air and powdered drug, as described in U.S. Pat. No. 5,577,497, incorporated herein by reference. The inhalation draws substantially all of the drug from the powder port 94 and air passage 92 into the mixing chamber 106, for inhalation. When inhalation is complete, the pressure switch 64 shuts off the motor 60. Inhalation preferably occurs when the slider is in the "out" position, when the blister is open and the inhaled air flow can draw any remaining drug out of the blister.

The patient next moves the slider 24 from the open position shown in FIG. 2 back to the closed position shown in FIG. 1. This movement is achieved by pushing on the slider front end 78. As the slider moves back into the closed position, the lifter 50 is pulled down on the ramp 72. The top surface 51 of the lifter 50 retracts to a position flush or below flush with the top surface of the deck plate 42. The cam profile of the lifter ramp 72 is designed to allow the lifter 50 to return to its neutral (down) position before the blister disk is incrementally advanced. The tab return spring 35 exerts a downward force on the tab, to push the tab back into a horizontal orientation. The tab return spring also helps to keep the disk flat against the deck, by exerting a downward spring force on the disk. The cover hub 188 also exerts a downward force on the disk as well.

At the same time, the advancing finger 84 moves into the advance slot 44 and flexes or springs upwardly. The flat back surface 85 of the advancing finger protrudes upwardly through the advance slot 44 and extends into a tab slot 154 on the blister disk 34. Continued closing movement of the slider 24 drives the advancing finger to rotate the disk 34. The blister crushing rib 170 crushes down the conical point of the blister. This provides a visual indication through the transparent cover that the dose in that blister has been used and allows the patient to easily visually check the number of remaining doses on the disk. With the slider 24 completely moved back to the closed position, the advancing finger 84 turns the disk 34 through an angle which brings the next subsequent blister tab 150 into alignment with the lifer slot 46 and powder port 94.

As the disk advances by one position, the foot 175 of the anti-backup pawl 174 rides up and out of the slot 154 and then drops back down into the next slot. The flat front surface 177 of the foot prevents reverse (clockwise when view from above) movement, while the ramp 179 on the back surface allows the foot and pawl to temporarily deflect up to allow the disk to advance in the forward direction.

The flex circuit 36 provides electrical connections between the batteries 62, motor 60, switch 64, and other components, such as lamp indicators, microprocessor, memory chips, etc. The ribbon 128 on the flex circuit 36 allows the batteries and slider to remain electrically connected to the other fixed components, as the slider 24 is moved between open and closed positions. This motion can also be accomplished with flexible wires or cables.

The microprocessor controls the motor via the breath sensor; counts doses delivered; signals low battery voltage; checks battery voltage, and controls LEDS which indicate use conditions of the inhaler.

The in and out movement of the slider is simple and easily achieved by almost all patients. It also provides for a reliable and compact design. Inadvertent actuation is also largely eliminated.

Thus, an improved dry powder inhaler has been shown and described. Various changes and modifications may of course be made without departing from the spirit of the invention. The invention, therefore, should not be restricted, except by the following claims and their equivalents.

We claim:

1. An inhaler for pharmaceuticals, comprising:
   a housing;
   a slider slidably attached to the housing;
   a ramp attached to the slider, the ramp defining a cam profile;
   an advancing finger attached to the slider; and
   a lifter slidably attached to the housing and to the ramp, with the movement of the lifter following the cam profile of the ramp, as the slider slides into and out of the housing.

2. The inhaler of claim 1 further comprising a battery compartment in the slider.

3. The inhaler of claim 2 further comprising a flex circuit having a battery plate at the battery compartment of the slider, connecting to a circuitry area attached to the housing, via a flex ribbon.

4. The inhaler of claim 3 wherein the flex circuit includes electrical conductors extending through the battery plate, ribbon, and circuitry area, thereby providing continuous electrical contact between the circuitry area and the battery plate.

5. The inhaler of claim 3 further comprising a mixing chamber in the housing, a motor in the housing, with the motor electrically connected to the flex circuit.

6. The inhaler of claim 1 further comprising a mouthpiece attached to the housing.

7. An inhaler for pharmaceuticals, comprising:
   a deck plate having a first side and a second side;
   a spindle on the first side of the deck plate;
   a powder port, an advancing slot, and a lifter slot, adjacent to the powder port, each extending through the deck plate;
   a blister disk rotatably supported on the spindle, with the blister disk having a plurality of equally spaced apart openings;
   a slider attached to the deck plate and movable between a first position and a second position;
   a ramp on the slider;
   a lifter slidably mounted on a frame on the second side of the deck plate and on the ramp on the slider, the frame allowing the lifter to move only along a specific path of motion towards and away from the lifter opening; and an advancing arm on the slider biased upwardly against the second side of the deck plate and aligned with the advancing opening.

8. The inhaler of claim 7 wherein the advancing arm converts linear motion of the slider to rotational motion of the blister disk.

9. An inhaler for pharmaceuticals, comprising:

a housing;

a slider on the housing movable between a first position and a second position;

an advancing finger on the slider;

a ramp and an advancing finger attached to the slider;

a lifter slidably attached to the housing and to the ramp; and a deck plate in the housing, the deck plate including an advance slot and a lifter slot, with the advancing finger passing through the advance slot when the slider is in the first position, and with the lifter passing through the lifter slot, when the slider is in the second position.

10. The inhaler of claim 9 wherein the deck plate has a top surface and a bottom surface, a spindle extending upwardly from the top surface for mounting a carrier disk, and a slider guide extending downwardly from the bottom surface, for guiding the slider.

11. The inhaler of claim 10 further comprising an lifter guide on the bottom surface of the deck plate, the lifter guide restraining the lifter in position, except along its path of motion.

12. The inhaler of claim 10 further comprising a first mechanical stop and a second mechanical stop on the housing for limiting travel of the slider into and out of the housing.

13. An inhaler for pharmaceuticals, comprising:

a deck plate;

a slider slidably attached to the deck plate;

a ramp and an advancing finger attached to the slider;

a lifter slidably attached to the deck plate and to the ramp; and a carrier disk rotatably supported on the deck plate, the carrier disk having a plurality of equally spaced apart openings and with a tab carrying a blister, the tab pivotally attached to the carrier disk within the openings.

14. The inhaler of claim 13, further comprising a cover attached to the carrier disk.

15. A dry powder inhaler, comprising:

a housing;

a slider slidable into and out of the housing;

a lifter slidably supported on a lifter rail on the housing; and means for vertically moving the lifter with horizontal movement of the slider.

* * * * *